United States Patent [19]

Weiss et al.

[11] Patent Number: 4,588,403
[45] Date of Patent: May 13, 1986

[54] VENTED SYRINGE ADAPTER ASSEMBLY

[75] Inventors: Merkel F. Weiss, Granada Hills; Joel C. Parrott, Valencia; Lisa Martel, Pasadena, all of Calif.

[73] Assignee: American Hospital Supply Corporation, Evanston, Ill.

[21] Appl. No.: 616,330

[22] Filed: Jun. 1, 1984

[51] Int. Cl.[4] .............................................. A61B 19/00
[52] U.S. Cl. .................................... 604/411; 604/414
[58] Field of Search ............... 604/405, 404, 403, 406, 604/407, 411, 412, 413, 414, 905, 126

[56] References Cited

U.S. PATENT DOCUMENTS

| 3,359,977 | 12/1967 | Burke | 604/414 |
| 4,211,588 | 7/1980 | Raines | 604/411 |
| 4,262,671 | 4/1981 | Kersten | 604/411 |

FOREIGN PATENT DOCUMENTS

| 80/02506 | 11/1980 | European Pat. Off. | 604/415 |
| 1307306 | 9/1962 | France | 604/411 |

*Primary Examiner*—John D. Yasko
*Attorney, Agent, or Firm*—Roger A. Williams

[57] ABSTRACT

A vented syringe adapter assembly which includes a housing having a sidewall, bottom wall, and top wall, which walls combine to define a chamber within the housing. A dual lumen tubular conduit extends through the top wall, chamber and bottom wall with one end extending from the top wall and defining a syringe connector port and the opposite end extending from the bottom wall and defining a piercing tip. A first lumen extends through the tubular conduit from the syringe port to the piercing tip. A second lumen extends from the piercing tip to the inner chamber. An opening is provided on at least one of the walls of the housing and the opening is covered by a filter for allowing the passage of gases but preventing the flow of liquids through the opening.

4 Claims, 3 Drawing Figures

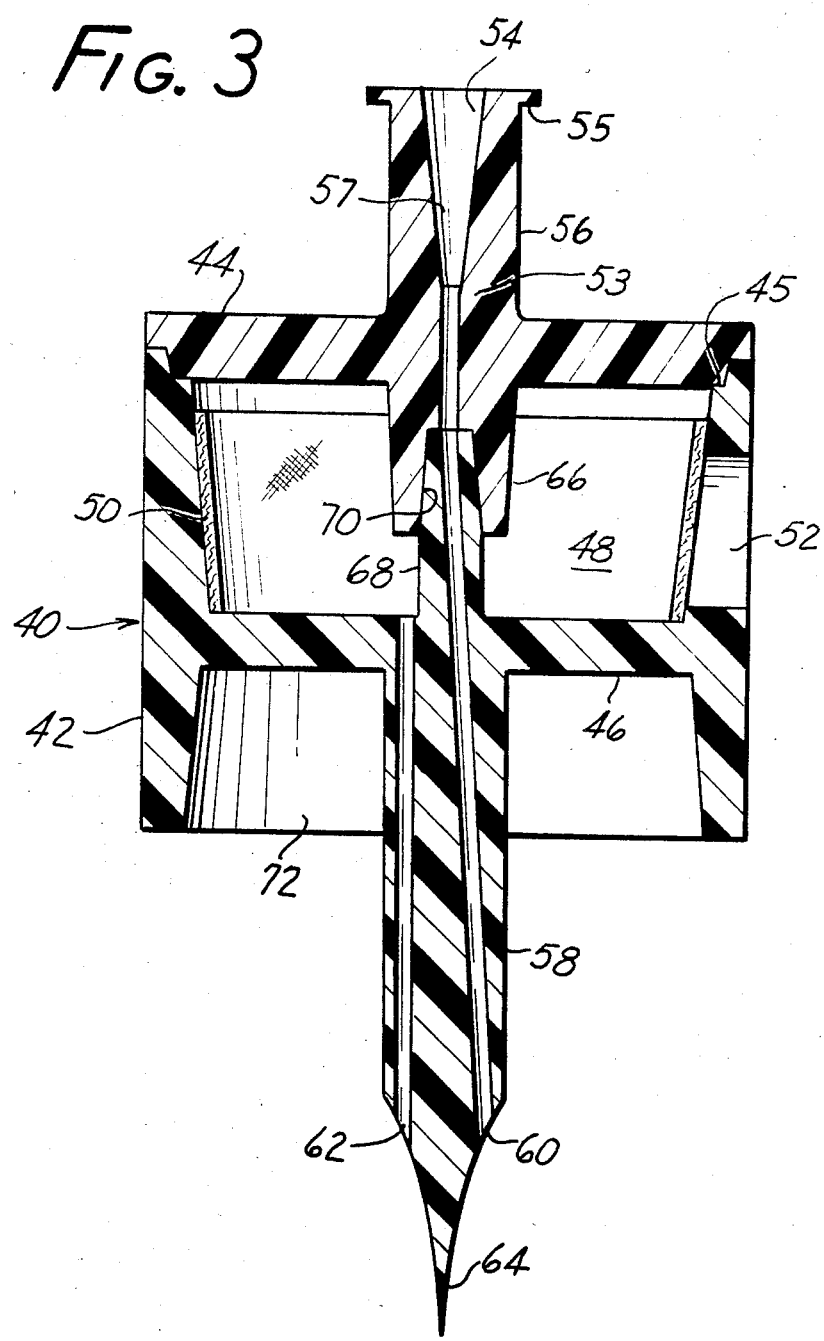

VENTED SYRINGE ADAPTER ASSEMBLY

BACKGROUND OF THE INVENTION

The invention herein is directed to a vented syringe adapter which is designed to prevent aerosolizing of liquid material picked up by the syringe and subsequently expelled from the syringe while removing entrapped air from the barrel of the syringe. Aerosolizing of certain medications routinely used in hospital environments can create hazards to the user. Certain chemotherapeutic drugs can be hazardous or dangerous, such as cytotoxic medications used for chemotherapy in the treatment of cancer. In some instances, many therapeutic drugs are supplied in a dry form or concentrated and need to be reconstituted or diluted in order to be administered. Reconstitution and dilution of such drugs can be performed with the use of a syringe, and during such procedures aerosolizing can occur. It is desirable for the person performing the procedures to avoid contacting the medications, especially the inhalation of aerosolized medications.

It would be desirable to provide a syringe adapter assembly which can be used in combination with a syringe and a medication vial and which would avoid aerosolizing of medications, such as hazardous chemotherapeutic drugs. It would be desirable to have such a syringe adapter assembly which would retain the potentially hazardous drug and would prevent the aerosolizing of such drug and possible inhalation thereof by the user.

SUMMARY OF THE INVENTION

The invention herein is a vented syringe adapter assembly which can be used in combination with a syringe. The assembly can be used with a syringe in the reconstituting of therapeutic drugs or while filling the syringe with a therapeutic drug, which therapeutic drug can be toxic or hazardous to the user. The use of the assembly herein prevents the aerosolizing of the drugs and thereby inhibits and prevents intimate contact of the user with such drug.

The assembly includes a housing having a sidewall, bottom wall, and top wall, all of which combine to define an inner chamber within the housing. Extending through the chamber and extending outwardly from the top wall and bottom wall is a dual lumen tubular conduit. The portion of the tubular conduit extending outwardly from the top wall includes a syringe connector port which coincides with and opens into a first lumen extending through the length of the tubular conduit. The portion of the tubular conduit extending outwardly from the bottom wall extends to form a sharp cannula tip which can pierce a perforable top of a standard medication container or vial. The first lumen extends through the tubular conduit and opens along such second projecting end adjacent the sharp cannula tip. A second lumen of the tubular conduit is open adjacent such sharp end of the tubular conduit and extends through the tubular conduit and opens intermediate the length of the tubular conduit into the chamber. An opening is provided along at least one of the walls of the housing, which opening is covered with a hydrophobic filter which permits venting of gases through the filter but prevents the flow of liquid and selected particle sizes. The vented syringe adapter assembly is constructed of plastic and, therefore, is readily disposable, which also provides inhibition or prevention of contamination from the assembly itself after it has been used as the assembly can be discarded.

BRIEF DESCRIPTION OF THE DRAWINGS

FIG. 3 is a cross-sectional elevational view of another embodiment of a vented syringe adapter assembly herein.

DETAILED DESCRIPTION

The vented syringe adapter assembly herein will be described with regard to the accompanying drawings. With regard to the drawings, the embodiment shown in FIGS. 1 and 2 is a preferred embodiment of the assembly herein, and the embodiment shown in FIG. 3 is an alternative embodiment of the assembly.

Figure 1:
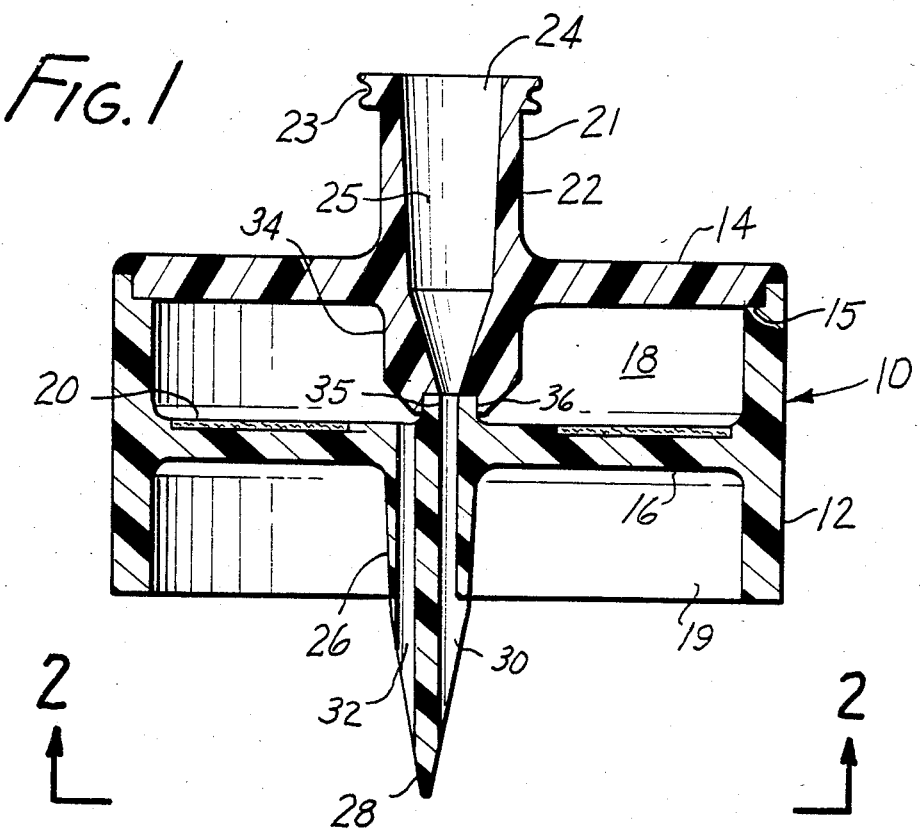
FIG. 1 is a cross-sectional elevational view of an embodiment of the vented syringe adapter assembly herein.
Figure 2:
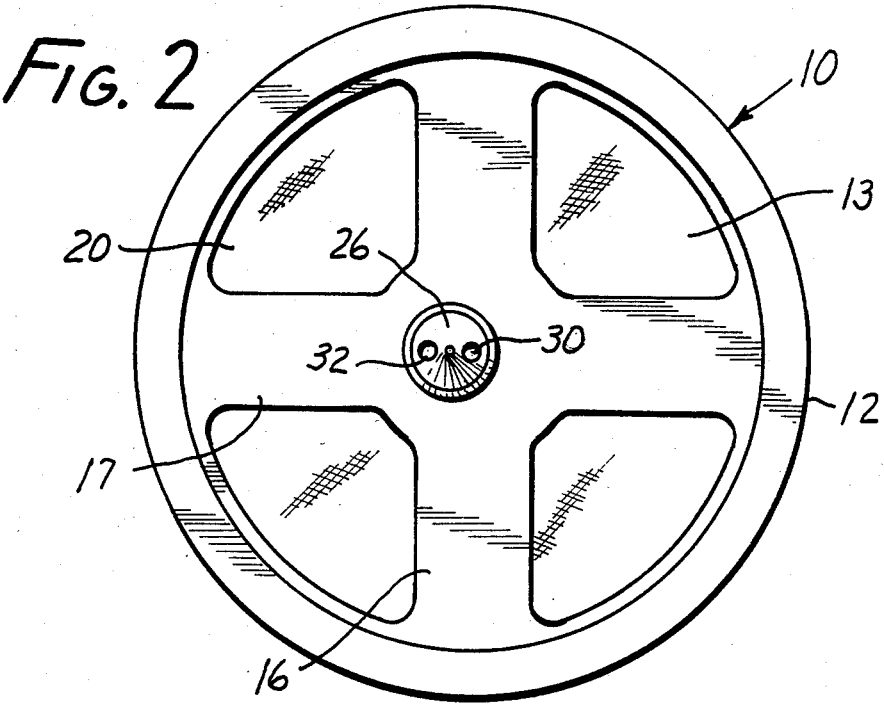
FIG. 2 is a bottom elevational view of the assembly shown in FIG. 1.

With reference to FIGS. 1 and 2, a vented syringe adapter assembly 10 is shown. The assembly includes a housing which is formed by a sidewall 12, a top wall 14, and a bottom wall 16. The housing can be of any geometric shape and, in the preferred embodiment, is shown as having a cylindrical shape with a cylindrical sidewall 12 and a circular bottom and top walls. The sidewall 12 can extend beyond the bottom wall as is shown in FIG. 1, forming a skirt on the housing. The skirt forming portion of the sidewall forms a recess 19 in the housing.

The sidewall, top wall, and bottom wall combine to form a chamber 18 within the housing. The chamber 18 provides a trap for aerosols which can be formed upon use of the assembly. The chamber 18 is vented through a vent opening extending through at least one of the walls. In the preferred embodiment, a plurality of vent openings 13 are provided on the bottom wall 16. The vent opening is covered or protected by a filter 20 which is a microporous filter that prevents the passage of liquids. A preferred filter is a hydrophobic filter which prevents the passage of about 0.2 micron size particles and liquids. As can be seen in FIG. 2, the filter element 20 can extend across the bottom wall 16 of the assembly, but be open through the provided openings 13 defined and separated by radially extending portions 17 of the bottom wall. The filter rests in a circular recess 11 on the chamber side of the bottom wall.

Extending through the chamber, top wall, and bottom wall of the assembly is a dual lumen tubular conduit 21. A first portion 22 of the tubular conduit extends outwardly from the top wall 14 of the housing to form a syringe connector. The first portion 22 is open and defines a syringe port 24 which can receive the hub of a syringe. The first portion 22 can also be provided with a locking means for locking the syringe to the first portion. For example, such locking means can be a standard male Luer locking thread 23. A second portion 26 of the tubular conduit 21 extends outwardly from the bottom wall and forms a puncture tip or piercing tip 28. The piercing tip 28 is a sharpened point which is sufficiently sharp to penetrate the perforable caps on medication vials.

A first lumen 30 extends through the length of the tubular conduit and is open through the syringe port 24 and through an opening adjacent the piercing tip 28. The first lumen has an opening greater than the opening for the second lumen to provide increased aspiration of fluid from an inverted vessel or container; i.e., medication vial, into which the piercing tip is inserted to give a syringe connected to the syringe port. A second lumen 32 extends partly through the tubular conduit. The second lumen 32 extends from an opening adjacent the piercing tip 28 and opens into the chamber 18 through an opening intermediate the length of the tubular conduit. The second lumen provides a vent from the medication vial to the chamber.

The assembly can be constructed in two parts as is shown in FIG. 1. The two parts are constructed of any convenient material, but preferably are constructed of a plastic such that the entire assembly is disposable. The two component assembly lends itself to being easily manufactured, such as by injection molding. In such a two-piece arrangement, one piece can include the top wall and first portion of the tubular conduit while the second portion can include the sidewall, bottom wall, and second portion of the tubular conduit. The two portions can be mated together and sealingly bonded such as through sonic welding, adhesive bonding, and the like. As shown in FIG. 1, the first section can be mated to the second by the provided recess or lip 15 on the sidewall. For such a two-piece assembly, the tubular conduit includes a third portion 34 associated with the top wall which extends into the chamber and mates with a fourth portion 35 associated with the bottom wall. In such an arrangement, the third and fourth portions of the tubular conduit can also be sealingly mated, such as through sonic welding. Thus, the first conduit is formed and retains its integrity with regard to fluid passage throughout its length.

With regard to FIG. 3, an alternative embodiment of the vented syringe adapter assembly 40 is shown. In the embodiment shown in FIG. 3, there is a sidewall 42, top wall 44, and bottom wall 46. The sidewall can depend or extend beyond the bottom wall to form a skirt encircling a cavity or recess 72. The sidewall, top wall, and bottom wall combine to form a chamber 48. The chamber 48 is open through the sidewall through a vent opening 52. Additional vent openings can be provided along the sidewall. A cylindrical-shaped hydrophobic filter 50 is provided within the chamber. The filter is positioned against the sidewall, and thus forms a barrier between the vent opening 52 and the chamber 48. If additional vent openings 52 are provided on the sidewall, then the filter 50 also provides a barrier.

The assembly 40 includes a dual lumen tubular conduit 53 which forms a syringe port 54 and a piercing tip 64 at its opposite ends. The tubular conduit is a dual lumen conduit with a first lumen 60 extending the length of the tubular conduit from the piercing tip to the syringe port and a second lumen 62 extending from the piercing tip to the chamber 48 intermediate the length of the tubular conduit.

The end of the tubular conduit extending from the top wall can also include means for locking and engaging a syringe hub, such as a Luer lock assembly 55 on a syringe connector portion 56 of the tubular conduit.

The assembly 40 shown in FIG. 3 can also be formed from two separate pieces. These two pieces can be mated and sealed together by bonding. The first portion can include the syringe connector portion 56 of the tubular conduit and the top wall 44. The second portion can include the bottom wall, sidewall, and piercing tip portion 58 of the tubular conduit. A third portion 66 of the tubular conduit associated with the top wall can have a recess 70 which mates with a fourth portion 68 of the tubular conduit associated with the bottom wall. The two portions of the housing can be mated, such as through a cooperating lip 45.

The vented syringe adapter assembly is used by connecting a syringe (not shown) to the syringe port. The assembly then is inserted into a medication vial containing a liquid medication desired to be introduced to the syringe. The syringe plunger is withdrawn drawing the medication up into the syringe. If air is present in the barrel of the syringe, the assembly can be inverted and the air evacuated by depressing the plunger of the syringe. During such an operation, any medication which is also expelled from the syringe is trapped in the vial, or any aerosolized medication evacuated from the vial is trapped in the chamber by the hydrophobic filter.

The assembly can also be used in reconstituting certain medications. In such an event, a syringe is connected to the assembly and fluid is introduced to the medication vial through the syringe. Air can be evacuated from the vial through the second lumen of the tubular conduit. Any entrained medication is trapped in the chamber by the filter. That is, the air can pass through the filter but any entrained droplets of the medication become trapped in the filter. In the unlikely event that there is some aerosolization around the puncture made by the piercing tip, such aerosolization is trapped in the skirted recess formed in the housing or at least directed away from the user by such a skirted housing. The recess or cavity formed by the skirt portion of the sidewall is deep enough to receive the neck of the medication vial.

We claim:

1. A vented syringe adapter assembly comprising:
   a first housing portion comprising a single lumen tubular conduit and a generally circular planar surface extending outwardly from and between the ends of the single lumen tubular conduit such that the lumen extends centrally through the first housing portion, the single lumen tubular conduit including syringe connector means on a first end and a recess on its second end through which the centrally extending lumen opens;
   a second sidewall housing portion comprising a generally cylindrical sidewall, a planar surface having provided openings therethrough, which planar surface extends across and joins the cylindrical sidewall, and a dual lumen tubular conduit extending through the planar surface generally parallel to the cylindrical sidewall with one of the lumens extending centrally through the second housing portion, wherein a first end of the dual lumen tubular conduit extends to define a piercing tip with both lumens opening therealong and second end which includes an opening for the centrally extending lumen and which second end extends to coincide with the recess on the second end of the single lumen tubular conduit, the second lumen of the dual lumen tubular conduit opens on the planar surface of such second housing portion, the second housing portion further comprising a circular recess on the planar surface, the first housing portion and second housing portions being interconnectable such that the circular planar surface of the first housing portion interconnects to the cylindrical sidewall of the second housing portion to form a chamber defined by the planar surface of the first housing portion and cylindrical surface and planar surface of the second housing portion and such that the second end of the dual lumen tubular conduit interconnects with the recess on the second end of the single lumen tubular conduit to provide one lumen extending through the combined first and second housing portions and one lumen opening into the chamber; and a generally circular hydrophobic filter provided in the recess on the circular planar surface of the second portion, which hydrophobic filter extends over the provided openings.

2. An assembly as recited in claim 1 wherein the cylindrical sidewall extends beyond the planar surface to form a skirt extending around the projecting piercing tip of the tubular conduit.

3. An assembly as recited in claim 1 wherein the first and second housing portions are comprised of plastic.

4. A vented syringe adapter assembly as recited in claim 1 further comprising an annular recess on the end of the cylindrical sidewall of the second housing portion in which recess the planar surface of the first housing portion of the housing can be interconnected.

* * * * *